United States Patent
Ziolo et al.

(10) Patent No.: US 7,955,364 B2
(45) Date of Patent: Jun. 7, 2011

(54) VARIABLE ANGLE BONE FIXATION ASSEMBLY

(75) Inventors: Tara Ziolo, Boonton, NJ (US);
Takkwong R Leung, Piscataway, NJ (US)

(73) Assignee: EBI, LLC, Parsippany, NJ (US)

( * ) Notice: Subject to any disclaimer, the term of this patent is extended or adjusted under 35 U.S.C. 154(b) by 1156 days.

(21) Appl. No.: 11/232,375

(22) Filed: Sep. 21, 2005

(65) Prior Publication Data

US 2007/0083207 A1   Apr. 12, 2007

(51) Int. Cl.
*A61B 17/86* (2006.01)

(52) U.S. Cl. .......................... 606/308; 606/291

(58) Field of Classification Search ............ 606/69–73, 606/300, 301, 305, 307, 291, 308; 411/347, 411/551, 554, 388–389, 380
See application file for complete search history.

(56) References Cited

U.S. PATENT DOCUMENTS

| | | |
|---|---|---|
| 2,248,054 A | 7/1941 | Decker |
| 2,293,930 A | 8/1942 | Braendel |
| 2,580,821 A | 1/1952 | Nicola |
| 2,780,223 A | 2/1957 | Haggland |
| 3,741,205 A | 6/1973 | Markolf et al. |
| 4,279,249 A | 7/1981 | Vert et al. |
| 4,388,921 A | 6/1983 | Sutter et al. |
| 4,463,753 A | 8/1984 | Gustilo |
| 4,473,068 A | 9/1984 | Oh |
| 4,484,570 A | 11/1984 | Sutter et al. |
| 4,655,203 A | 4/1987 | Tormala et al. |
| 4,743,257 A | 5/1988 | Tormala et al. |
| 4,903,691 A | 2/1990 | Heinl et al. |
| 4,905,680 A | 3/1990 | Tunc |
| 5,053,036 A | 10/1991 | Perren et al. |
| 5,057,109 A | 10/1991 | Olerud et al. |
| 5,080,665 A | 1/1992 | Jarrett et al. |
| 5,108,399 A | 4/1992 | Eitenmuller et al. |
| 5,129,903 A | 7/1992 | Luhr et al. |
| 5,139,498 A | 8/1992 | Astudillo Ley et al. |
| 5,147,360 A | 9/1992 | Dubousset et al. |
| 5,180,381 A | 1/1993 | Aust et al. |
| 5,275,601 A | 1/1994 | Gogolewski et al. |
| 5,290,281 A | 3/1994 | Tschakaloff et al. |
| 5,346,492 A | 9/1994 | Morgan |
| 5,364,399 A | 11/1994 | Lowery et al. |

(Continued)

FOREIGN PATENT DOCUMENTS

DE    4343117    6/1995

(Continued)

OTHER PUBLICATIONS

Partial European Search Report, EP06019645, Mar. 10, 2008, European Patent Office.

*Primary Examiner* — Eduardo C Robert
*Assistant Examiner* — Elana B Fisher
(74) *Attorney, Agent, or Firm* — Harness, Dickey

(57) ABSTRACT

A bone fixation assembly and associated method. The bone fixation assembly includes a bone fastener having a shaft for engaging a bone, and a head connected to the shaft. The shaft defines a longitudinal first axis. The bone fastener also includes a plurality of external thread windings defining an outer surface of the head. The external thread windings are circumferentially interrupted by at least one slot defined on the outer surface. The slot is inclined at an angle relative to the first axis.

13 Claims, 3 Drawing Sheets

U.S. PATENT DOCUMENTS

| | | | |
|---|---|---|---|
| 5,376,102 A | 12/1994 | Jarrett et al. | |
| 5,423,826 A | 6/1995 | Coates et al. | |
| 5,456,719 A | 10/1995 | Keller et al. | |
| 5,468,242 A | 11/1995 | Reisberg et al. | |
| 5,520,690 A | 5/1996 | Errico et al. | |
| 5,531,746 A | 7/1996 | Errico et al. | |
| 5,569,250 A | 10/1996 | Sarver et al. | |
| 5,578,034 A | 11/1996 | Estes | |
| 5,578,046 A | 11/1996 | Liu et al. | |
| 5,601,553 A | 2/1997 | Trebing et al. | |
| 5,607,426 A | 3/1997 | Ralph et al. | |
| 5,607,427 A | 3/1997 | Tschakaloff et al. | |
| 5,607,428 A | 3/1997 | Lin | |
| 5,676,666 A | 10/1997 | Oxland et al. | |
| 5,681,311 A | 10/1997 | Foley et al. | |
| 5,690,631 A | 11/1997 | Duncan et al. | |
| 5,702,396 A | 12/1997 | Hoenig et al. | |
| 5,704,936 A | 1/1998 | Mazel et al. | |
| 5,707,372 A | 1/1998 | Errico et al. | |
| 5,709,686 A | 1/1998 | Talos et al. | |
| 5,713,898 A | 2/1998 | Stucker et al. | |
| 5,713,900 A | 2/1998 | Benzel et al. | |
| 5,718,705 A | 2/1998 | Sammarco | |
| 5,735,853 A | 4/1998 | Olerud et al. | |
| 5,766,176 A | 6/1998 | Duncan | |
| 5,797,914 A | 8/1998 | Leibinger et al. | |
| 5,800,433 A | 9/1998 | Benzel et al. | |
| 5,814,048 A | 9/1998 | Morgan | |
| 5,843,082 A | 12/1998 | Yuan et al. | |
| 5,868,746 A | 2/1999 | Sarver et al. | |
| 5,876,402 A | 3/1999 | Errico et al. | |
| 5,904,683 A | 5/1999 | Pohndorf et al. | |
| 5,925,048 A | 7/1999 | Ahmad et al. | |
| 5,954,722 A | 9/1999 | Bono | |
| 5,961,524 A | 10/1999 | Crombie | |
| 5,980,540 A | 11/1999 | Bruce | |
| 6,001,101 A | 12/1999 | Augagneur et al. | |
| 6,019,763 A | 2/2000 | Nakamura et al. | |
| 6,036,693 A | 3/2000 | Yuan et al. | |
| 6,039,740 A | 3/2000 | Olerud et al. | |
| 6,090,111 A | 7/2000 | Nichols | |
| 6,117,173 A | 9/2000 | Taddia et al. | |
| 6,129,730 A | 10/2000 | Bono et al. | |
| 6,147,135 A | 11/2000 | Yuan et al. | |
| 6,152,927 A | 11/2000 | Farris et al. | |
| 6,179,839 B1 | 1/2001 | Weiss et al. | |
| 6,193,721 B1 | 2/2001 | Michelson | |
| 6,206,881 B1 | 3/2001 | Frigg et al. | |
| 6,206,883 B1 | 3/2001 | Tunc | |
| 6,214,008 B1 | 4/2001 | Illi et al. | |
| 6,221,075 B1 | 4/2001 | Tormala et al. | |
| 6,228,085 B1 | 5/2001 | Theken et al. | |
| 6,235,033 B1 | 5/2001 | Brace et al. | |
| 6,241,771 B1 | 6/2001 | Gresser et al. | |
| 6,261,291 B1 | 7/2001 | Talaber et al. | |
| 6,273,899 B1 | 8/2001 | Kramer | |
| 6,290,703 B1 | 9/2001 | Ganem et al. | |
| 6,294,187 B1 | 9/2001 | Boyce et al. | |
| D449,692 S | 10/2001 | Michelson | |
| 6,306,140 B1 * | 10/2001 | Siddiqui | 606/315 |
| 6,322,562 B1 | 11/2001 | Wolter et al. | |
| 6,331,179 B1 | 12/2001 | Freid et al. | |
| 6,361,537 B1 | 3/2002 | Anderson | |
| 6,383,186 B1 | 5/2002 | Michelson | |
| 6,398,783 B1 | 6/2002 | Michelson | |
| 6,402,756 B1 | 6/2002 | Ralph et al. | |
| 6,402,757 B1 | 6/2002 | Moore, III et al. | |
| 6,402,759 B1 | 6/2002 | Strong et al. | |
| 6,413,259 B1 | 7/2002 | Lyons et al. | |
| 6,416,528 B1 | 7/2002 | Michelson | |
| 6,423,068 B1 | 7/2002 | Reisberg et al. | |
| 6,428,542 B1 | 8/2002 | Michelson | |
| 6,440,135 B2 | 8/2002 | Orbay et al. | |
| 6,440,136 B1 | 8/2002 | Gambale et al. | |
| 6,454,769 B2 | 9/2002 | Wagner et al. | |
| 6,458,133 B1 | 10/2002 | Lin | |
| 6,503,250 B2 | 1/2003 | Paul | |
| 6,547,790 B2 | 4/2003 | Harkey, III et al. | |
| 6,572,622 B1 | 6/2003 | Schafer et al. | |
| 6,585,769 B1 | 7/2003 | Muhanna et al. | |
| 6,595,993 B2 | 7/2003 | Donno et al. | |
| 6,599,290 B2 | 7/2003 | Bailey et al. | |
| 6,610,062 B2 | 8/2003 | Bailey et al. | |
| 6,620,163 B1 | 9/2003 | Michelson | |
| 6,623,486 B1 | 9/2003 | Weaver et al. | |
| 6,645,208 B2 | 11/2003 | Apfelbaum et al. | |
| 6,669,701 B2 | 12/2003 | Steiner et al. | |
| 6,689,134 B2 | 2/2004 | Ralph et al. | |
| 6,702,817 B2 | 3/2004 | Beger et al. | |
| 6,709,686 B1 | 3/2004 | Matthew | |
| 6,716,214 B1 | 4/2004 | Jackson | |
| 6,719,759 B2 | 4/2004 | Wagner et al. | |
| 6,730,091 B1 * | 5/2004 | Pfefferle et al. | 606/70 |
| 6,761,719 B2 | 7/2004 | Justis et al. | |
| 6,767,351 B2 * | 7/2004 | Orbay et al. | 606/287 |
| 6,786,909 B1 | 9/2004 | Dransfeld et al. | |
| 6,893,444 B2 | 5/2005 | Orbay | |
| 6,916,320 B2 | 7/2005 | Michelson | |
| 2001/0012940 A1 | 8/2001 | Tunc | |
| 2002/0045896 A1 | 4/2002 | Michelson | |
| 2002/0065517 A1 | 5/2002 | Paul | |
| 2002/0077630 A1 | 6/2002 | Lin | |
| 2002/0120268 A1 | 8/2002 | Berger | |
| 2002/0120273 A1 | 8/2002 | Needham et al. | |
| 2002/0183755 A1 | 12/2002 | Michelson | |
| 2003/0018335 A1 | 1/2003 | Michelson | |
| 2003/0105462 A1 | 6/2003 | Haider | |
| 2003/0153919 A1 | 8/2003 | Harris | |
| 2003/0225409 A1 | 12/2003 | Freid et al. | |
| 2004/0039387 A1 | 2/2004 | Gause et al. | |
| 2004/0044345 A1 | 3/2004 | DeMoss et al. | |
| 2004/0068319 A1 | 4/2004 | Cordaro | |
| 2004/0073218 A1 * | 4/2004 | Dahners | 606/69 |
| 2004/0127896 A1 | 7/2004 | Lombardo et al. | |
| 2004/0153092 A1 | 8/2004 | Beger et al. | |
| 2004/0181228 A1 | 9/2004 | Wagner et al. | |
| 2004/0236332 A1 | 11/2004 | Frigg | |
| 2004/0260291 A1 * | 12/2004 | Jensen | 606/69 |
| 2005/0165400 A1 | 7/2005 | Fernandez | |
| 2005/0277937 A1 * | 12/2005 | Leung et al. | 606/69 |
| 2006/0009771 A1 * | 1/2006 | Orbay et al. | 606/69 |

FOREIGN PATENT DOCUMENTS

EP  1570796  9/2005

* cited by examiner

VARIABLE ANGLE BONE FIXATION ASSEMBLY

INTRODUCTION

In certain orthopedic surgical procedures, it is necessary to secure multiple bones or bone portions relative to each other. For example, in spinal surgeries, the fusion of two or more vertebral bodies is required to secure a portion of the spinal column in a desired position. Portions of other bones of the human body can be similarly joined. This need may be the result of physical trauma from fractures or dislocations, degenerative diseases, or tumors.

Various plating systems for internal fixation of various bones are known. Such systems generally include a plate that is attached to the bone or bone portions spanning a fracture line or a spinal disc space. The plate typically includes a plurality of holes through which bone screws are inserted for engaging the bone.

Some plating systems include constrained or locking screws, which are adapted for locking in corresponding plate holes in a fixed orientation. Other plating systems include semi-constrained or non-locking screws, which can be configured to maintain a variable orientation relative to the plate. Examples of plating systems that include constrained and semi-constrained screws are disclosed in currently pending, co-owned U.S. patent application Ser. No. 11/023,096, filed Dec. 22, 2004, and Ser. No. 11/124,535, filed May 5, 2005. The disclosures of these applications are incorporated herein by reference. A plating system that includes a locking ring that prevents the screw from backing out of the plate is disclosed in commonly owned U.S. Pat. No. 6,599,290, the disclosure of which is incorporated herein by reference.

Although the existing plating systems can be satisfactory for their intended purposes, there is still a need for new plating systems that are effective and efficient and also provide operative simplicity and versatility to the surgeon.

SUMMARY

The present teachings provide a bone fixation assembly that includes a bone fastener. The bone fastener includes a shaft for engaging a bone and a head connected to the shaft. The shaft defines a longitudinal first axis. The bone fastener also includes a plurality of external thread windings defining an outer surface of the head. The external thread windings are circumferentially interrupted by at least one slot defined on the outer surface. The slot is inclined at an angle relative to the first axis.

The present teachings also provide a bone fixation assembly that includes a fixation member having a threaded aperture, and a bone fastener having a head and an anchoring portion. The head includes circumferentially interrupted external threads such that the head can engage the aperture at an angle by controlled angled-threading.

The present teachings also provide a method for securing a bone fastener to a bone fixation member. The method includes providing a bone fastener defining a first axis, the bone fastener having a bone anchoring portion and a head having an external thread thereon, providing a bone fixation member defining at least one aperture having an internal thread, the aperture defining a second axis, inserting the bone fastener through the aperture, and securing the head of the bone fastener to the aperture such that the first axis is inclined relative to the second axis.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, the present teachings can be used for, but are not limited to, fusion procedures of adjoining bones, such as vertebrae, and/or for internal fixation of fractures in any bones.

Figure 1:
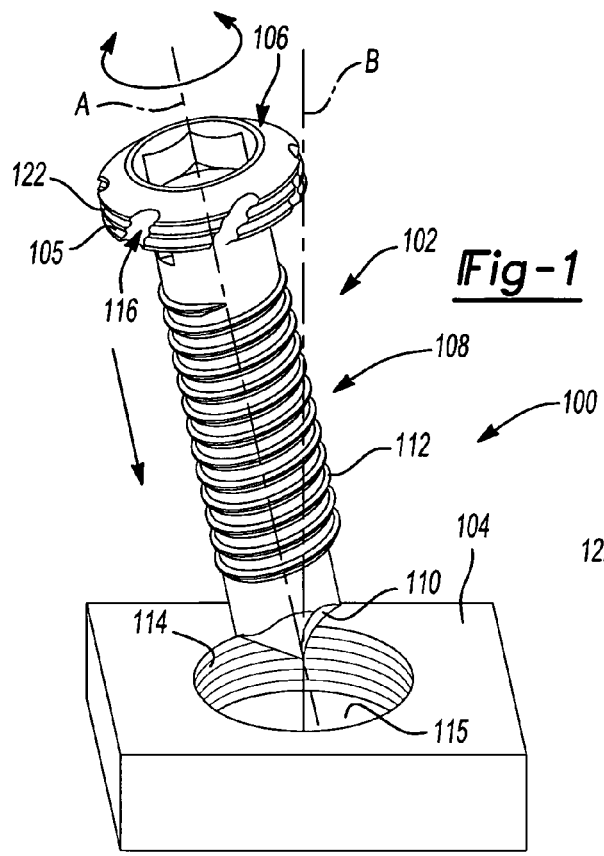
FIG. 1 is a perspective view of a bone fixation assembly according to the present teachings, shown before assembly.

Referring to FIG. 1, an exemplary bone fixation assembly 100 according to the present teachings is illustrated before assembly. The bone fixation assembly 100 can include a bone fastener 102 defining a longitudinal axis "A", and a fixation member 104. The fixation member 104 can be a planar body, such as a plate, or a curved generally two-dimensional body adapted to be positioned adjacent or against a bone surface for securing, stabilizing, or fusing a bone or bone portions to each other. The fixation member 104 can include one or more through-holes or apertures 115 having a center axis "B". Each aperture 115 can include internal threads 114. The aperture 115 or at least the threaded portion thereof can be spherical.

Figure 3:
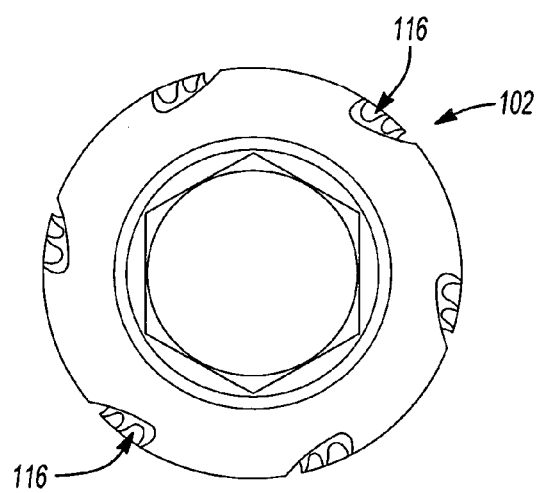
FIG. 3 is a top end view of the bone fastener of FIG. 2.
Figure 2:
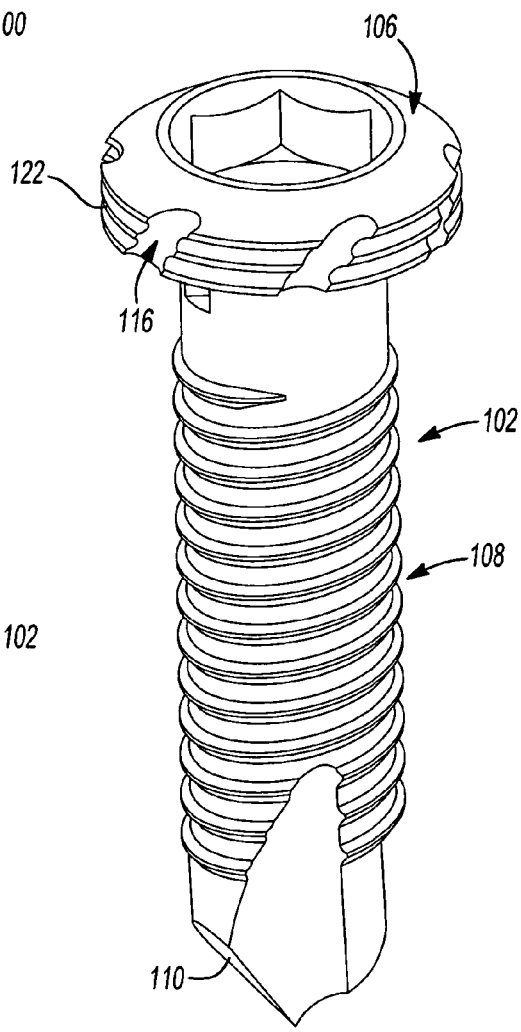
FIG. 2 is a perspective view of a bone fastener of the bone fixation assembly of FIG. 1.
Figure 4:
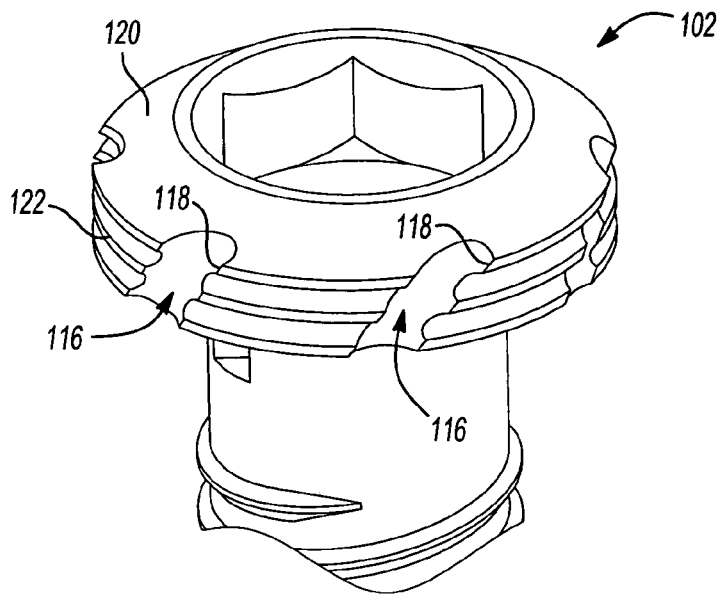
FIG. 4 is a top end perspective view of the bone fastener of FIG. 2.

Referring to FIGS. 1-4, the bone fastener 102 can include a head 106 and a bone anchoring portion 108, such as a shaft, terminating at a distal tip 110. The anchoring portion 108 can include a helical or other type of thread 112. The diameter of the head 106 can be larger than the diameter of the bone anchoring portion 108. The head 106 can include an engagement formation 130 for engaging a driver or other insertion tool (not shown) to the head 106 for inserting the bone fastener 102 into bone. The head 106 can have a convex curved lateral or outer surface 105, which can be, for example, spherical, and adapted for engagement with a similarly shaped portion of the aperture 115. The outer surface 105 can include a thread having external threads (thread windings) 122 that are circumferentially interrupted by one or more slots 116. Although six slots 116 are illustrated in FIG. 3, it will be appreciated that the number of slots 116 can vary. The slots 116 can be inclined/skewed relative to the thread windings 122 and relative to the longitudinal axis A of the bone fastener 102. For example, the slots 116 can be inclined at an angle relative to the longitudinal axis A ranging from zero (parallel to the longitudinal axis A) to about 70 degrees. The slots 116 can be shaped and oriented such that when the head 106 is threaded to the aperture 115, any soft tissue remaining on the fixation member 104 is removed and directed through the slots 116 away from aperture 115 and the bone fixation site. The slots 116 can define, for example, cutouts 120, and tissue-cutting or tissue-removing edges 118, as shown in FIG. 4, for clearing the aperture 115 of tissue. The slots 116 can also be shaped and oriented to guide the bone fastener 102 for variable angle fixation relative to the fixation member 104, as discussed below.

Referring to FIGS. 1 and 5-7, the bone fastener 102 can be inserted into the aperture 115 such that the axes A and B coincide, or such that the axes A and B define a variable angulation angle α, as desired by the surgeon. When the axes A and B are made to coincide, the external threads 122 of the head 106 can engage the internal threads 114 of the aperture 115 without angled-threading, i.e. with each single internal thread winding 114 engaging a single external thread winding 122 and conversely. When the axes A and B are positioned at an angle, the slots 116 provide a form of controlled and guided "angled-threading", such that a single internal thread winding 114 can engage portions of more than one external thread winding 122 at an angle, and conversely. For example, each slot 116 can be of a width and orientation such that when the bone fastener 102 is rotated at an angle relative to the axis B of the aperture 115, an internal thread winding 114 that becomes initially engaged with a particular external thread winding 122 encounters the slot 116 and disengages from that particular external thread winding 122. The shape (including size) and orientation of the slots 116 can be selected for controlling and guiding the angled-threading such that there is no damage to the external or internal thread windings 122, 114. Such damage is sometimes associated with unintentional and undesirable cross-threading.

Figure 5:
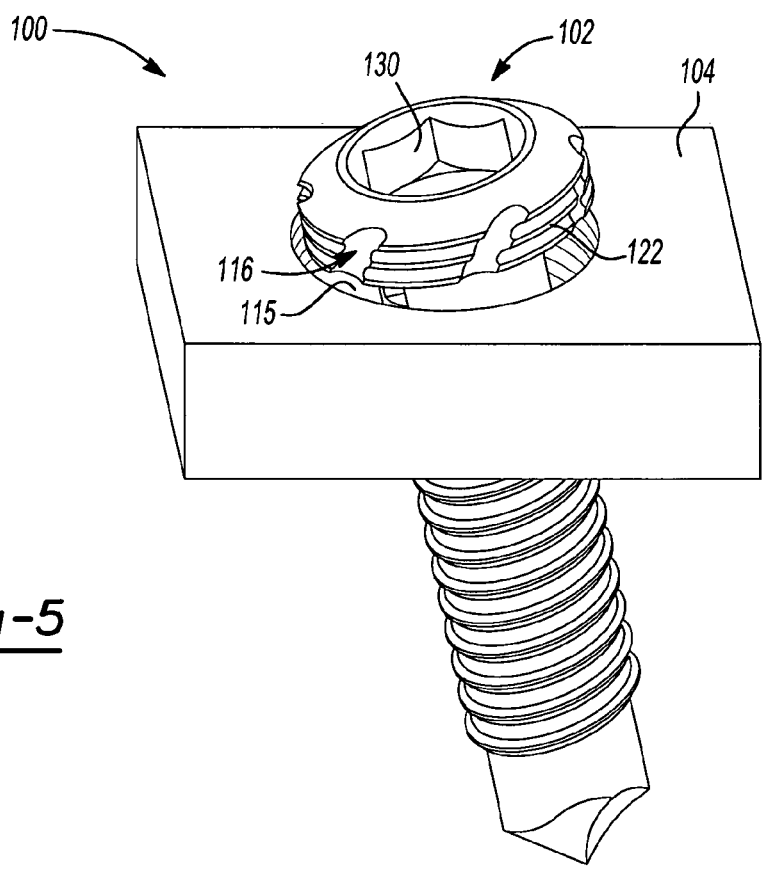
FIG. 5 is a perspective view of the bone fixation assembly of FIG. 1, shown partially assembled.
Figure 6:
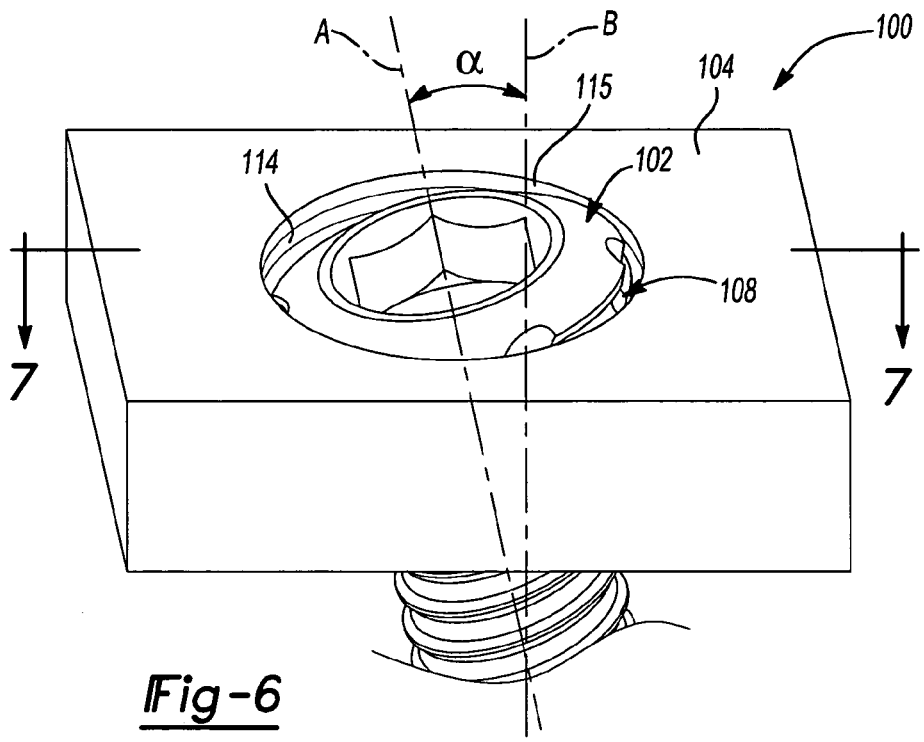
FIG. 6 is a perspective view of the bone fixation assembly of FIG. 1, shown fully assembled.
Figure 7:
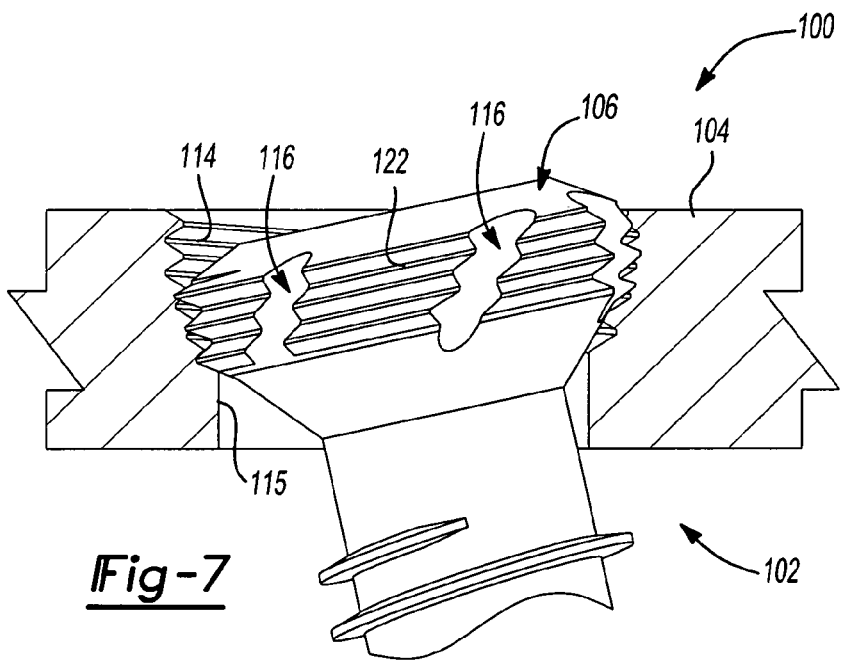
FIG. 7 is a sectional view of the bone fixation assembly of FIG. 1, shown fully assembled.

As illustrated in FIG. 1, the bone fastener 102 can be oriented at a desired angle relative to the fixation member 104 and inserted through the aperture 115 into bone. Referring to FIG. 5, rotating the fastener 102 with a driver or other insertion tool, gradually drives the anchoring portion 108 into the bone, while the edges 118 of the slots 116 remove any tissue from the aperture 115, and guide removed tissue along the slots 116 away from the aperture 115. After any such tissue is removed, the external threads 122 of the head 108 engage the internal threads 114 of the aperture 115 at an angle, as discussed above, securing and locking the bone fastener 102 at an angled position relative to the fixation member 104, as shown in FIGS. 6 and 7. Variable angle fixation and self-locking are, therefore, effected by the fastening mechanism that includes the circumferentially interrupted external threads 122 on the outer surface 105 of the head 106 of the bone fastener 102, without need of additional components or parts, thereby simplifying the surgical procedure.

As described above, the bone fixation assembly provides the surgeon with the option of anchoring the bone fastener 102 at a desired angle relative to the fixation member 104, while clearing tissue from the aperture 115 of the fixation member 104, thereby providing clean engagement surfaces for locking the bone fastener 102 to the fixation member 104.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:
1. A bone fixation assembly comprising:
a unitary bone fastener comprising a shaft for engaging a bone, the shaft defining a longitudinal first axis;
a head extending from the shaft; and
a plurality of external thread windings formed on a substantially spherical outer surface of the head, the external thread windings circumferentially interrupted by at least one slot defined on the outer surface, the slot inclined at an angle relative to the first axis and relative to the thread windings; and
a fixation member comprising at least one aperture having a second axis, the aperture comprising internal thread windings formed on a substantially spherical portion of the aperture for threadably engaging the had of the bone fastener at a variable angle relative to the second axis, the at least one slot shaped and sized for guiding the fastener for controlled angled threading within the aperture without damaging the internal thread windings of the aperture.

2. The bone fixation assembly of claim 1, wherein the bone fastener and the aperture can be threadably engaged in first and second positions, such that in the first position the first and second axes are substantially coincident, and such that in the second position the first and second axes define a variable angle therebetween.

3. The bone fixation assembly of claim 2, wherein in the second position the external and internal thread windings are engaged such that at least one external thread winding engages a portion of a first internal thread winding before encountering the at least one slot and, after encountering the at least one slot, the at least one external thread winding disengages from the portion of the first internal thread winding and engages a portion of second internal thread winding.

4. The bone fixation assembly of claim 2, wherein in the second position the external and internal thread windings are engaged such that at least one internal thread winding engages portions of at least two external thread windings one at a time.

5. The bone fixation assembly of claim 1, wherein the slot is shaped and oriented at a nonzero angle relative to the thread windings for guiding soft tissue away from the aperture.

6. The bone fixation assembly of claim 1, wherein the slot is shaped and oriented for engaging the fastener at an angle relative to the second axis.

7. The bone fixation assembly of claim 1, wherein a perimeter of the aperture in the fixation member is similar to an outer circumference of the head of the bone fastener.

8. The bone fixation assembly of claim 1, wherein the internal windings of the fixation member are generally continuous.

9. A bone fixation assembly comprising:
a fixation member having an aperture with a substantially spherical threaded portion; and
a unitary bone fastener having a head extending from an anchoring portion, the head having a substantially spherical outer surface and a plurality of external threads formed on the spherical outer surface of the head, the head including a plurality of slots interrupting the external threads, the slots inclined at a nonzero angle relative to the external threads for controlling angled-threading between the head and the aperture, such that the head can engage the aperture at an angle without damage to the threaded portion of the aperture.

10. The bone fixation assembly of claim 9, wherein the head includes a driver engagement formation.

11. The bone fixation assembly of claim 9, wherein a perimeter of the aperture in the fixation member is similar to an outer circumference of the head of the bone fastener.

12. The bone fixation assembly of claim 9, wherein the internal windings of the fixation member are generally continuous.

13. A bone fixation assembly comprising:
- a bone fastener comprising:
  - a shaft for engaging a bone, the shaft defining a longitudinal first axis;
  - a head connected to the shaft; and
  - a plurality of external thread windings formed on a substantially spherical outer surface of the head, the external thread windings circumferentially interrupted by at least one slot defined on the outer surface, the slot inclined at an angle relative to the first axis and relative to the thread windings; and
- a fixation member comprising at least one aperture having a second axis, the aperture comprising internal thread windings formed on a substantially spherical portion of the aperture for threadably engaging the head of the bone fastener at a variable angle relative to the second axis, the at least one slot shaped and sized for guiding the fastener for controlled angled threading within the aperture without damaging the internal thread windings of the aperture;
- wherein the bone fastener and the aperture can be threadably engaged in first and second positions, such that in the first position the first and second axes are substantially coincident, and such that in the second position the first and second axes define a variable angle therebetween; and
- wherein in the second position the external and internal thread windings are engaged such that at least one external thread winding engages a portion of a first internal thread winding before encountering the at least one slot and, after encountering the at least one slot, the at least one external thread winding disengages from the portion of the first internal thread winding and engages a portion of second internal thread winding.

* * * * *

UNITED STATES PATENT AND TRADEMARK OFFICE
CERTIFICATE OF CORRECTION

| | | |
|---|---|---|
| PATENT NO. | : 7,955,364 B2 | Page 1 of 1 |
| APPLICATION NO. | : 11/232375 | |
| DATED | : June 7, 2011 | |
| INVENTOR(S) | : Tara Ziolo et al. | |

It is certified that error appears in the above-identified patent and that said Letters Patent is hereby corrected as shown below:

Column 1
Line 27, "application" should be --applications--

Column 4
Line 13 (claim 1) "had" should be --head--

Signed and Sealed this
Second Day of August, 2011

David J. Kappos
*Director of the United States Patent and Trademark Office*